(12) United States Patent
Burgeson et al.

(10) Patent No.: US 11,382,998 B2
(45) Date of Patent: Jul. 12, 2022

(54) SCENT DEVICE

(71) Applicant: WILDLIFE RESEARCH CENTER, INC., Ramsey, MN (US)

(72) Inventors: Samuel A. Burgeson, Andover, MN (US); Anthony Berg, White Bear Lake, MN (US)

(73) Assignee: Wildlife Research Center, Inc., Ramsey, MN (US)

(*) Notice: Subject to any disclaimer, the term of this patent is extended or adjusted under 35 U.S.C. 154(b) by 117 days.

(21) Appl. No.: 16/720,234

(22) Filed: Dec. 19, 2019

(65) Prior Publication Data

US 2021/0187145 A1 Jun. 24, 2021

(51) Int. Cl.
*A61L 9/12* (2006.01)
*B01D 53/04* (2006.01)
(Continued)

(52) U.S. Cl.
CPC .............. *A61L 9/12* (2013.01); *A01M 31/00* (2013.01); *A61L 9/014* (2013.01);
(Continued)

(58) Field of Classification Search
CPC ... A61L 9/04; A61L 9/12; A61L 9/127; A61L 2209/10; A61L 2209/13; A61L 2209/131;
(Continued)

(56) References Cited

U.S. PATENT DOCUMENTS 1,916,982 A * 7/1933 Jones .................. A01M 1/2055
43/131
6,126,085 A 10/2000 Wanzenboeck
(Continued)

FOREIGN PATENT DOCUMENTS

CN 203169651 U 9/2013
CN 203354961 U 12/2013
(Continued)

OTHER PUBLICATIONS

"DIY Lighted Potpourri Jar." Published Oct. 20, 2015. <<https://www.pinkwhen.com/diy-lighted-potpourri-jar/>> Accessed Aug. 19, 2021. (Year: 2015).*

(Continued)

*Primary Examiner* — Timothy C Cleveland
(74) *Attorney, Agent, or Firm* — Dorsey & Whitney LLP (57) ABSTRACT

A scent device comprises a container defining a volume and configured to hold a fill material, which may include one or more chemical compounds, natural formulations, or both configured to absorb odor and/or moisture, and/or emit a scent. The scent device includes a vented cap reversibly coupled to the container via a connection mechanism, and a breathable insert sandwiched between the container and the cap. The breathable insert may comprise a non-woven fabric supported along its perimeter by a structural mount. Methods of manufacturing the scent device involve cutting a mount from a support material, attaching a breathable material to the mount to form a breathable insert, depositing a scent-controlling material within a container, and sandwiching the breathable insert between the container and a cap upon coupling the cap with the container.

10 Claims, 13 Drawing Sheets

(51) Int. Cl.
*B01D 53/26* (2006.01)
*A61L 9/014* (2006.01)
*A01M 31/00* (2006.01)

(52) U.S. Cl.
CPC ....... *B01D 53/0407* (2013.01); *B01D 53/261* (2013.01); *A61L 2209/15* (2013.01); *A61L 2209/22* (2013.01); *B01D 2257/80* (2013.01); *B01D 2257/90* (2013.01)

(58) Field of Classification Search
CPC ........... A61L 2209/133; A61L 2209/15; A61L 2209/22; A01M 31/00; A01M 31/008; B01D 53/0407; B01D 53/261; B01D 2257/80; B01D 2257/90
See application file for complete search history.

(56) References Cited

U.S. PATENT DOCUMENTS

| | | | |
|---|---|---|---|
| 6,213,409 | B1 | 4/2001 | Warren et al. |
| 6,371,453 | B1* | 4/2002 | Hunter ..................... A61L 9/12 |
| | | | 261/107 |
| 6,398,127 | B1 | 6/2002 | Wingo |
| 6,857,579 | B2 | 2/2005 | Harris |
| 7,528,102 | B2 | 5/2009 | Barthel et al. |
| 2002/0197187 | A1 | 12/2002 | Murray |
| 2003/0012680 | A1 | 1/2003 | Balsys |
| 2005/0014668 | A1 | 1/2005 | Bariou et al. |
| 2005/0246938 | A1 | 11/2005 | Windus |
| 2008/0011870 | A1 | 1/2008 | Link et al. |
| 2017/0035162 | A1 | 2/2017 | Leshem |
| 2018/0140736 | A1 | 5/2018 | Webb |

FOREIGN PATENT DOCUMENTS

| | | |
|---|---|---|
| DE | 10303352 A1 | 8/2004 |
| DE | 202008003630 | 7/2008 |
| GB | 2324963 | 11/1998 |
| JP | 2005040207 A | 2/2005 |
| JP | 2019023106 A | 2/2019 |
| KR | 20170055285 A | 5/2017 |
| WO | 2009144674 A2 | 12/2009 |
| WO | 2017153287 A1 | 9/2017 |

OTHER PUBLICATIONS

"4 Pack Stainless Steel Sprouting Jar Strainer Lids." Mar. 21, 2019. <<https://www.amazon.com/Pack-Stainless-Steel-Sprouting-Strainer/dp/B07NM9TNXP/ref=sr_1_6?dchild=1&keywords=mason+jar+strainer+lids&qid=1629398300&s=home-garden&sr=1-6>>. Accessed Aug. 19, 2021. (Year: 2019).*

Jillee, "How to Make 3 Naturally Scented Air Fresheners for Cars" blog post, Bright Ideas, posted on Jan. 28, 2017, 28 pages, retrieved from https://www.onegoodthingbyjillee.com/how-to-make-3-naturally-scented-air-fresheners-for-cars/.

* cited by examiner

SCENT DEVICE

TECHNICAL FIELD

The present disclosure relates to scent devices and associated methods of manufacture. Implementations include methods of manufacturing a scent device comprised of a breathable insert coupled with an odor-controlling container and vented cap.

BACKGROUND

A large variety of scent devices are available for a wide range of purposes in both indoor and outdoor settings. For example, animal attraction devices configured to emit natural scents are often employed by hunters. Air fresheners are frequently used indoors to mask unpleasant odors, and heat-resistant devices are occasionally placed in driers to improve the smell of freshly washed clothes. Despite their effectiveness in certain contexts, preexisting devices are often confined to narrow uses, vulnerable to changing environmental conditions, and limited by rigid manufacturing parameters. New devices are needed to improve the versatility, durability and effectiveness of scent devices without adding complexity to their associated methods of manufacture.

SUMMARY

Implementations disclosed herein provide scent devices configured to improve, eliminate, or otherwise control odors in various indoor or outdoor settings. In accordance with some examples of the present disclosure, a scent device may include a container defining a volume and configured to hold a fill material. The scent device may also include a cap reversibly coupled to the container via a connection mechanism and a breathable insert sandwiched between the container and the cap. The breathable insert may comprise a support mount defining a central aperture and attached to a perimeter of a breathable material.

In some examples, the cap may define one or more vents, each vent defining an opening in the cap that exposes the breathable insert. In some embodiments, the breathable material of the breathable insert comprises a non-woven fabric. In some examples, the connection mechanism comprises a snap-fit mechanism. In some embodiments, the fill material comprises one or more chemical compounds, natural formulations, or both configured to absorb odor and/or moisture, and/or emit a scent. Examples of the fill material can include activated carbon, crystals, powders, and/or gel beads, one or more of which may be scented. In some examples, the scent device further includes a suspension mechanism configured to suspend the container above a surface. In some embodiments, the breathable insert may have a cross-sectional thickness of about 0.01 to about 0.05 inches. In some embodiments, the container may have a diameter of about 2 to about 5 inches. In some examples, the fill material may be configured to attract one or more wild animals.

In accordance with some examples of the present disclosure, methods of manufacturing a scent device may involve cutting a mount from a support material, attaching a breathable material to the mount to form a breathable insert, depositing a scent-controlling material within a container defining a volume, and sandwiching the breathable insert between the container and a cap upon coupling the cap with the container.

In some examples, the scent-controlling material comprises a composition configured to absorb moisture, absorb odor, emit a scent, or combinations thereof. In some embodiments, the breathable material comprises a non-woven fabric. In some examples, the support material comprises pulp board, paper board and/or foam. In some embodiments, attaching the breathable material to the mount comprises laminating the breathable material to one side of the mount, which may or may not also include a surface adhesive. In some examples, cutting the mount from the support material comprises using a die apparatus to cut the mount from a roll of the support material. In some embodiments, the breathable insert may have a cross-sectional thickness of about 0.01 to about 0.05 inches. In some examples, the support material may be substantially rigid. In some embodiments, the support material may comprise a double-sided adhesive. In some examples, sandwiching the breathable insert between the container and the cap may involve applying a side of the mount opposite the breathable material to a lip portion of the container. In some embodiments, coupling the cap with the container comprises snap-fitting the cap to the container.

DETAILED DESCRIPTION

Implementations provide scent devices configured for a variety of uses. Embodiments of the scent device can include a container reversibly coupled with a cap and configured to hold a scent-controlling fill material, such as scented crystals or activated carbon. A breathable insert comprised of non-woven fabric, for example, may be sandwiched between the container and the cap. The pores of the breathable insert can be configured to allow consistent, controlled release of one or more aromatic compounds emitted from the fill material, and/or the absorption of odor and/or moisture from the surrounding air. The cap can define one or more open portions, or vents, to expose the underlying breathable insert. The scent device can be employed for both indoor and outdoor uses, for example for air freshening, moisture absorption, scent elimination or scent emitting.

Novel, scalable methods of manufacturing the scent device are also disclosed. Example methods can involve forming a mount or backing from a stock supply of support material, e.g., pulp board or foam, to provide a support structure for a breathable insert. One side of the mount can be attached to a perimeter portion of the breathable material of the insert, for example via lamination and/or an adhesive. The container can be filled, entirely or partially, with the scent-controlling fill material. After filling the container, the breathable insert can be sandwiched between the cap and the container as the two components are coupled together.

As used herein, the term "scent device" includes devices configured as scent dispensers, air fresheners, scent eliminators, odor absorbers, moisture absorbers, animal attractants, clothing fresheners, etc. The shape, dimensions, and fill material of the disclosed scent devices may be adjusted to achieve different purposes. For consistency and ease of illustration, the term "scent" is used throughout this disclosure to describe assorted scents, odors, fragrances or scent-eliminating aromatics released from the disclosed scent devices. As used herein, a "scent-controlling material" encompasses materials that emit a certain scent or fragrance, as well as materials that eliminate various odors and/or absorb moisture from the air.

Embodiments of the scent device described herein may include an approximately cylindrical container. Accordingly, select dimensions of the container may be referred to by the properly associated terms, e.g., "diameter." This should not be construed as limiting, as the scent-controlling containers described herein may have a wide variety of shapes, e.g., rectangular, irregular or substantially flat. The term "diameter" should thus be understood to encompass the analogous dimensions of other shapes, e.g., length or width.

Scent Device Product

Figure 1A:
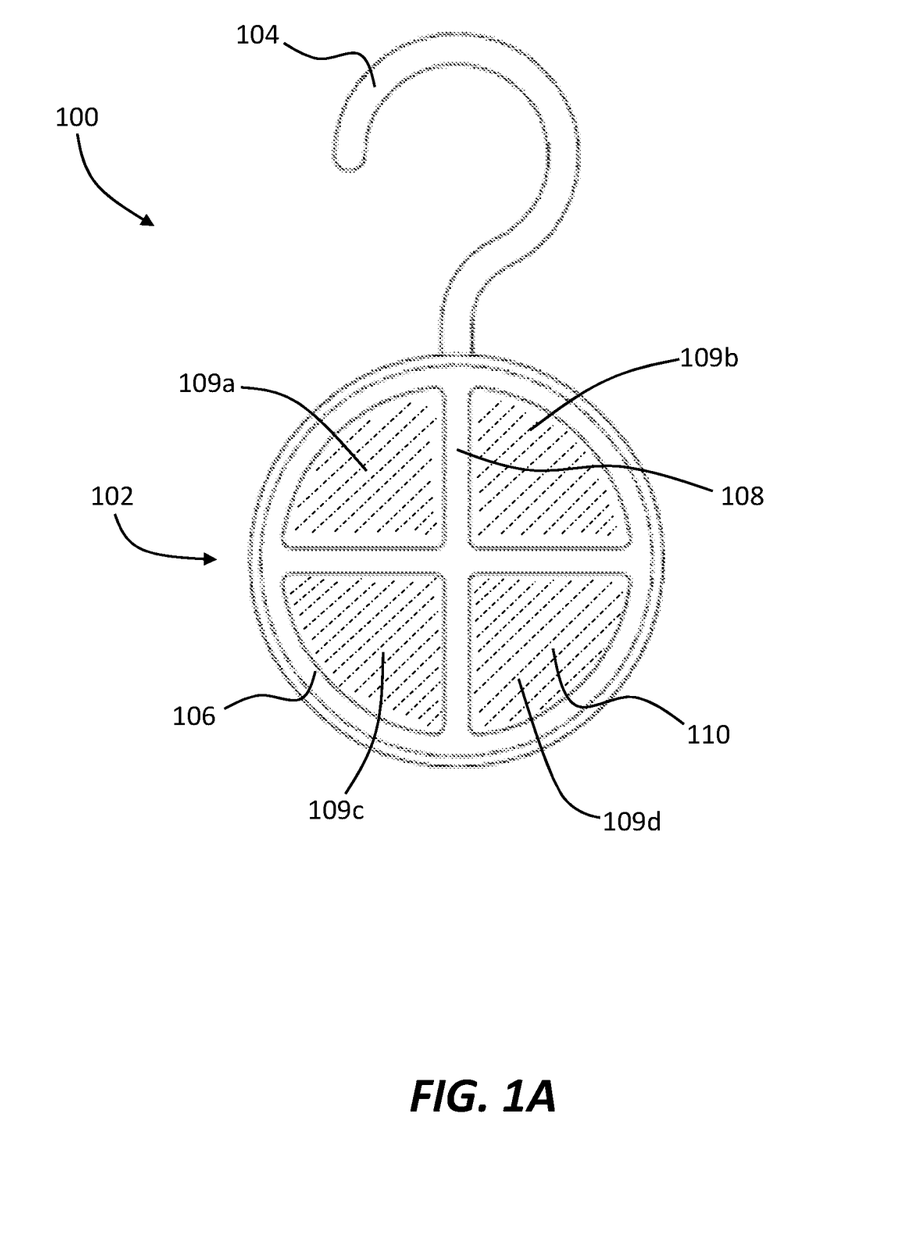
FIG. 1A is a plan view of a scent device in accordance with embodiments of the present disclosure.

FIG. 1A shows a plan view of an example scent device 100. As shown, the scent device 100 includes a container 102 attached to a hook 104. The container 102, or jar, is coupled with a cap 106, which features intersecting bars 108 extending across the container 102. A breathable insert 110 in the shape of a disk is visible between the bars 108, which together define four vents 109a-d in the scent device 100. In this embodiment, the breathable insert 110 is visible on only one side of the scent device 100, such that the opposite side (or bottom) of the device is closed. The breathability of the insert 110 allows scents emitted from a fill material held within the container 102 to escape at a consistent rate through the vents 109a-d to the surrounding environment. This breathability also enables consistent absorption of odors and/or moisture into the device 100.

The breathable insert 110 can be comprised of a support mount that defines a central aperture and is attached to a perimeter portion of a breathable material, such as a fabric, which may be non-woven to enhance breathability. Embodiments may also include breathable materials made of various woven fabrics, threaded polymers, and/or mesh. The pore sizes defined by the breathable material can dictate the rate of scent release from the scent device. The larger the pores, the faster the rate of scent release. A scent-controlling material, e.g., scented powder, may also be embedded directly within at least a portion of the breathable insert, which may vary in its cross-sectional thickness. In embodiments, the breathable insert may have a cross-sectional thickness of less than about 0.01 in., about 0.01 in., about 0.02 in., about 0.03 in., about 0.04 in., about 0.05 in., greater than about 0.05 in., or any thickness therebetween.

The hook 104 may be useful for outdoor uses, e.g., hunting operations, where optimal use of the scent device may be achieved by suspending the device above the ground. Examples may also include other suspension mechanisms. For example, the container 102 may be attached to a string or rope, which may be coupled with various structures. The container 102 may also include an adhesive on the surface opposite the exposed breathable insert 110. The scent device 100 may also include one or more magnetic elements such that it can be attached to various household appliances. The hook 104, and any other suspension mechanism, may also be excluded in some embodiments, for example embodiments in which the scent device 100 is simply placed on a flat surface.

The configuration of the bars 108 may vary and may depend on a number of factors. The mass of the fill material held within the container 102, the location at which the scent device 100 is typically used, and/or the desired rate of scent release may impact the configuration of the bars. For example, heavier fill material may necessitate a more comprehensive, concealing grid of bars 108 to provide the structural support necessary to maintain the integrity of the breathable insert 110, especially if the scent device 100 is suspended above the ground. Scent devices configured for outdoor use may also include a more comprehensive network of bars 108 to shield the fill material from weather effects. A more comprehensive configuration of bars 108 may also be utilized to achieve a slower rate of scent release by enclosing a greater surface area of the breathable insert 110. As further described below, the bars 108 may also be replaced by an adjustable cap. In some embodiments, the breathable material comprising the breathable insert 110 may be configured to match the venting scheme defined by the bars 108.

Figure 1B:
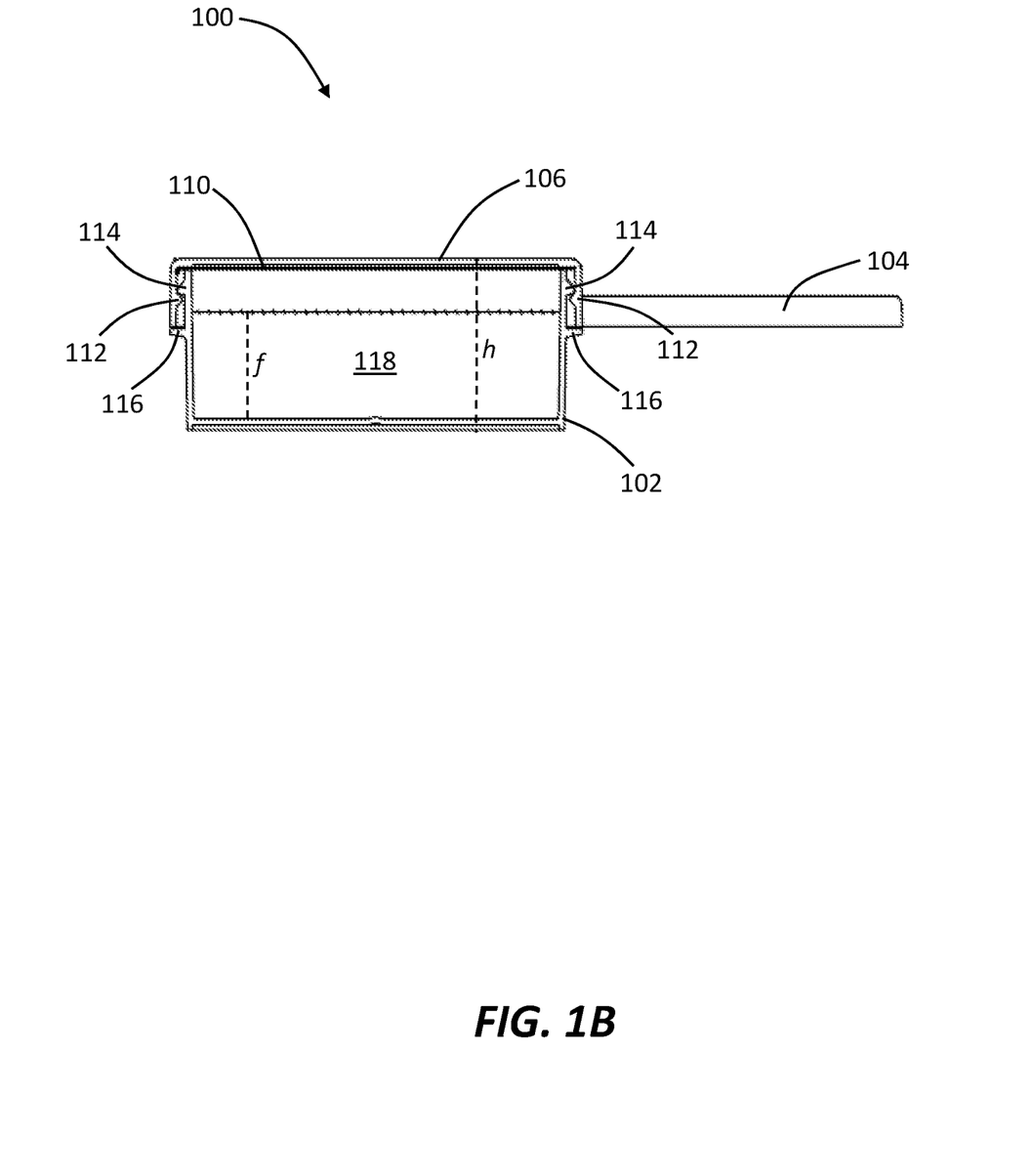
FIG. 1B is a cross-sectional side view of the scent device shown in FIG. 1A.

FIG. 1B shows a cross-sectional side view of the scent device 100, showing the container 102 and the hook 104. As shown, the breathable insert 110 may be sandwiched between the cap 106 and the container 102. In the illustrated example, the cap 106 is configured to couple with the container 102 via a snap-fit mechanism. Specifically, the cap 106 may define one or more protrusions 112 configured to reversibly engage one or more lip portions 114 defined by the container 102. Embodiments may feature one protrusion having a defined length, a plurality of protrusions spaced around the perimeter of the cap 106, or a single protrusion extending circumferentially around the entire cap perimeter. The container 102 may also define one or more complementary ledge portions 116 configured to contact a surface of the cap 106. The cap 106 may be relatively flexible such that the protrusion 112 may flex over the lip portion 114 of the container 102 when the cap 106 is urged onto and off of the container 102. After flexing, the cap 106 can return to its static position, in which the walls of the cap are approximately perpendicular with respect to each other.

The container 102 may accommodate various volumes of fill material 118. The fill material 118 reaches a fill level f, which may correspond to a volume of about 25 ml or less, about 25 ml, about 50 ml, about 75 ml, about 100 ml, about 125 ml, about 150 ml, about 175 ml, about 200 ml, about 300 ml, about 500 ml, more than about 500 ml, or any volume therebetween. Various fill materials may be included within the container 102. For example, the fill material 118 may include one or more chemical compounds, natural formulations, or both configured to absorb odor and/or moisture, and/or emit a scent. Non-limiting examples of the fill material 118 may include activated carbon, scented powder, scented gel beads, or scented crystals, just to name a few. The texture of the fill material 118 may be generally granular. The pore size of the breathable material comprising the breathable insert 110 may be selected in view of the particle size of the fill material 118 to prevent the fill material 118 from simply passing immediately through the breathable insert 110 when the scent device 100 is not placed on a flat surface with the vents 109a-d facing up. More refined materials, e.g., powders, may thus be matched with breathable inserts 110 comprised of a material having smaller pores.

The dimensions of the scent device 100 may vary depending on the configuration and materials comprising each component and the associated methods of assembly. For example, to prevent leakage and facilitate insertion of the breathable insert 110 between the container 102 and the cap 106, the breathable insert 110 may have a larger diameter than the container 102 and a smaller diameter than the cap 106, as shown in FIG. 1B. The exact shape and dimensions of the container 102 and cap 106 may vary. In the embodiment shown, the two components together form a generally cylindrical canister, but the container 102 and/or the cap 106 may also be approximately rectangular, tubular, flat, oblong or irregular in other examples. The dimensions of the device 100 may vary depending on the specific use or use location. For example, the scent device 100, particularly the container 102, may have larger dimensions for outdoor applications and smaller, more discreet dimensions for indoor applications. Larger containers may accommodate a greater amount of fill material, which may be preferable for outdoor or larger area applications. In various embodiments, the cap 106 may have a diameter ranging from less than about 2.5 in. to about 2.5 inches, or about 2.75 in., about 3.0 in., about 3.25 in., about 3.50 in., about 3.75 in., about 4.0 in., about 4.25 in., about 4.5 in., about 4.75 in., about 5.0 in., about 5.25 in., about 5.5 in., greater than about 5.5 inches, or any diameter therebetween. The container 102 may have a diameter ranging from less than about 2.0 in. to about 2.0 inches, or about 2.25 in., about 2.50 in., about 2.75 in., about 3.0 in., about 3.25 in., about 3.50 in., about 3.75 in., about 4.0 in., about 4.25 in., about 4.5 in., about 4.75 in., about 5.0 in., greater than about 5.0 inches, or any diameter therebetween. Non-cylindrical embodiments of the container 102 may have the same or similar widths and/or lengths. The height h of the container 102, when coupled with the cap 106, may also vary. In some examples, the height h may range from less than about 0.5 in. to about 0.5 in., about 0.75 in., about 1.0 in., about 1.25 in., about 1.5 in., about 1.75 in., about 2.0 in., about 2.25 in., about 2.5 in., more than 2.5 in., or any height therebetween.

Embodiments of the scent device 100 may be reusable or configured for one-time use. Single-use embodiments may come pre-loaded with the fill material 118. Examples in which the fill material 118 is configured to absorb odors and/or moisture may be especially amenable to single-use assembly and packaging. Single-use embodiments may feature a cap 106 that is not removable from the container 102.

For reusable applications, removal of the cap 106 from the container 102 can allow periodic replacement of the breathable insert 110 and/or the fill material 118. The scent device 100 shown in FIG. 1B features the snap-fit connection mechanism, but embodiments may include different connection mechanisms. For example, the cap 106 and container 102 may define complementary threaded portions configured to accommodate screwing of the cap 106 onto the container 102. The cap 106 can also be attached to the container 102 at one end via a hinge or latch member. The cap 106 can also be slid on and off the container 102, which can define lateral tracks configured to receive the cap 106.

Figure 2:
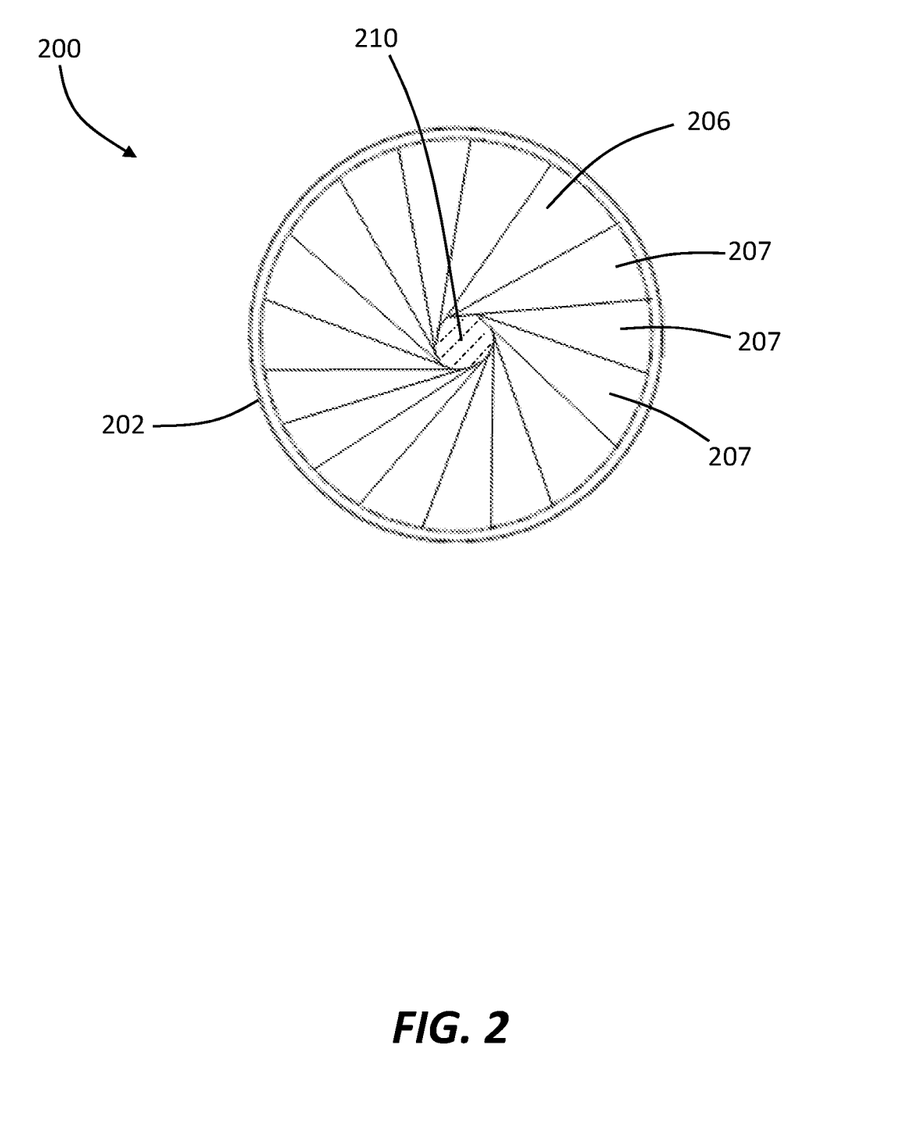
FIG. 2 is a plan view of another scent device in accordance with embodiments of the present disclosure.

FIG. 2 shows a scent device 200 that lacks a suspension mechanism, such that the device comprises container a 202 coupled with a cap 206, only. A portion of a breathable insert 210, again shaped as a disk, is exposed beneath the cap 206, which may be adjustable, such that the exposed surface area of the breathable insert 210 may shrink or expand depending on the configuration of the cap 206. In this embodiment, adjustment of the cap 206 is effected by movement of a plurality of panels 207. Rotation of the cap 206 with respect to the container 202 may cause the panels 207 to retract toward the perimeter of the cap 206. Rotation of the cap 206 in the opposite direction may cause the panels 207 to extend back toward the center of the cap.

Figure 3:
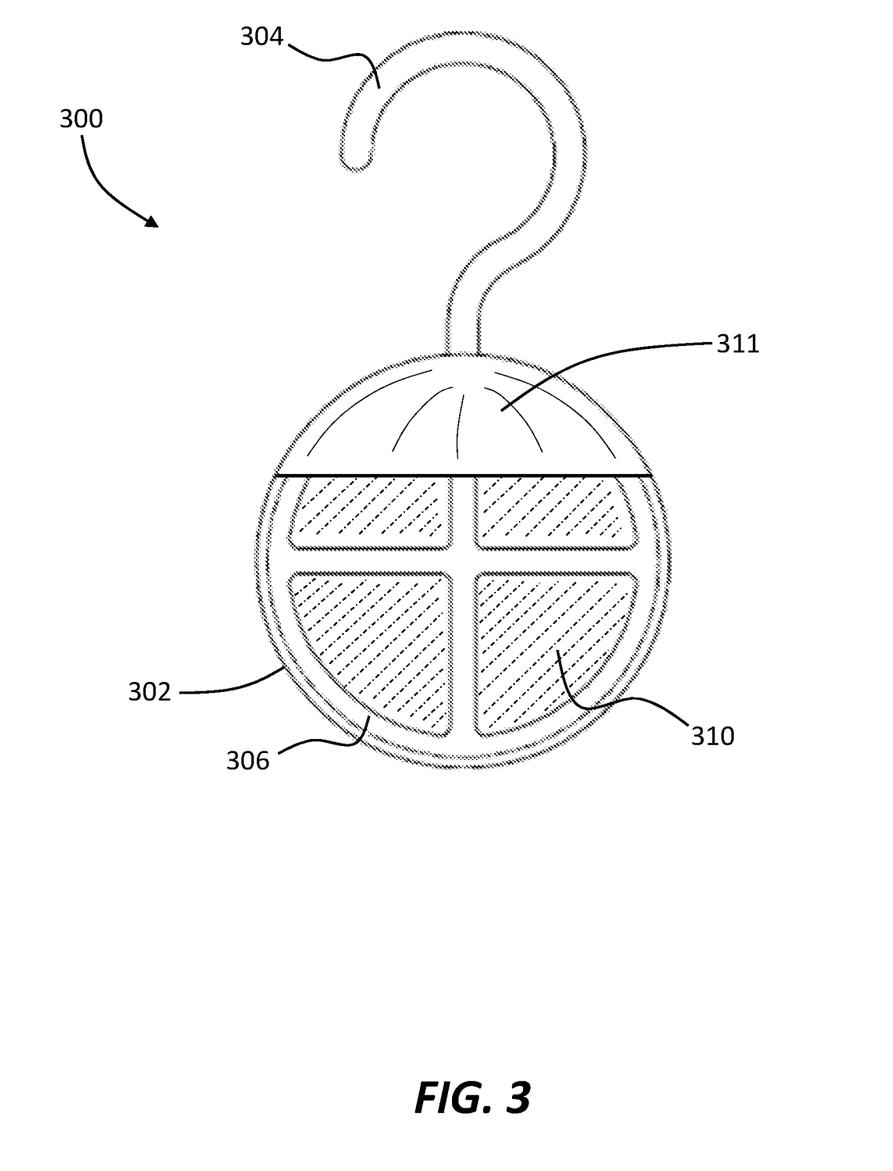
FIG. 3 is a plan view of another scent device in accordance with embodiments of the present disclosure.

FIG. 3 shows a scent device 300 that includes, in addition to a container 302, hook 304, cap 306 and breathable insert 310, a shield or cover 311 extending over a portion of the cap 306. The cover 311 may be included in embodiments equipped with suspension means and configured for outdoor use. When suspended above the ground from hook 304, the cover 311 may protect the exposed portions of breathable insert 310 from damaging weather effects and precipitation, such as wind, rain, snow and/or flying debris.

Figure 4:
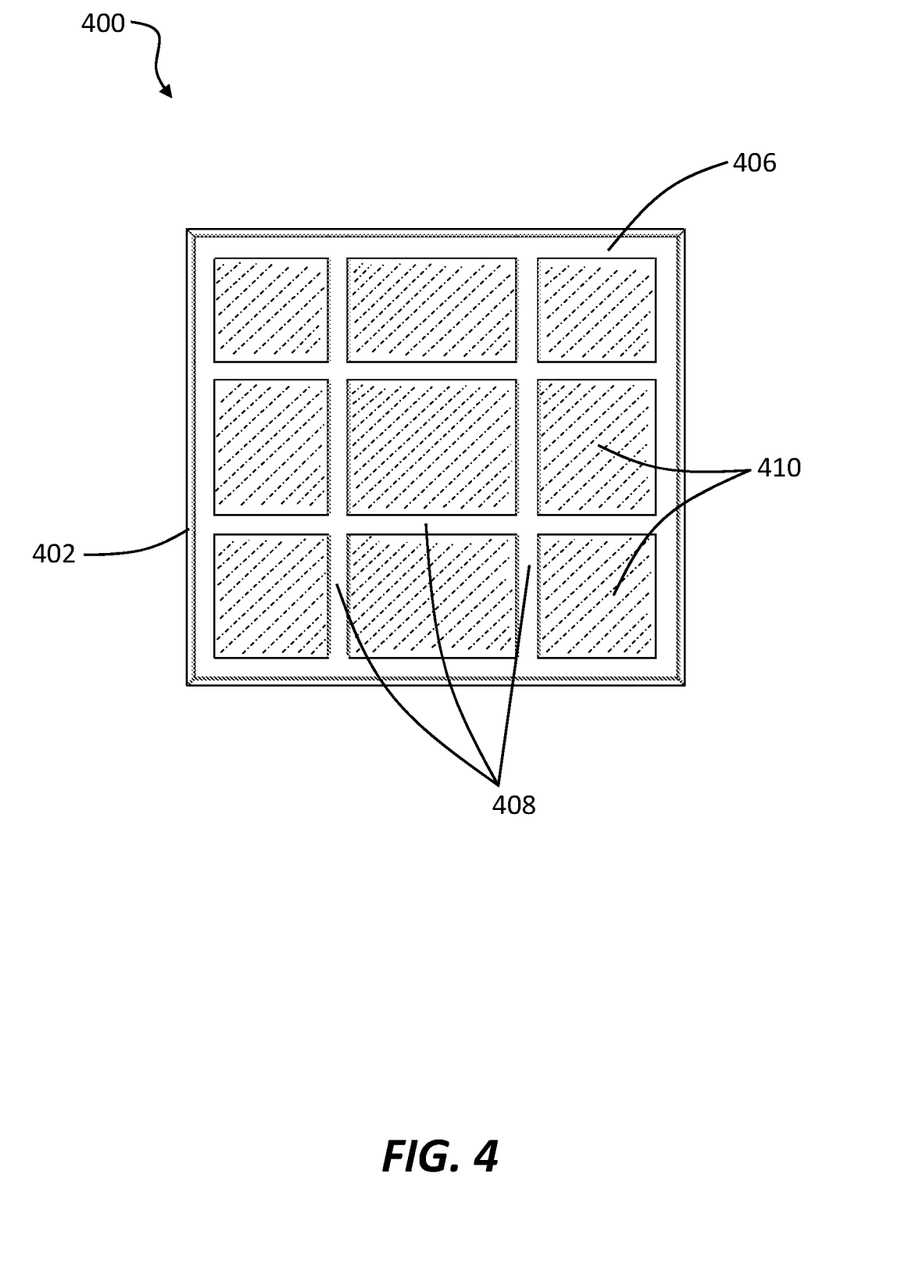
FIG. 4 is a plan view of another scent device in accordance with embodiments of the present disclosure.

FIG. 4 shows a scent device 400 that includes a rectangular container 402 coupled with a rectangular cap 406. In this example, the cap 406 includes four cross bars 408, which together define nine windows or vents through which an underlying, rectangular breathable insert 410 is visible. The scent device 400 may have a more narrow height than the scent device 100 shown in FIGS. 1A and 1B, making the scent device 400 especially well equipped for small or narrow spaces, e.g., in a duffle bag or between units of furniture and a wall. The rectangular scent device 400 represents just one additional example of an acceptable configuration for the scent devices described herein. It should be understood to those skilled in the art that the shape of the device may vary.

Methods of Manufacturing the Scent Device Product

FIGS. 5A-5G illustrate various steps in an example method of forming a scent device in accordance with embodiments described herein. While the fully assembled scent device comprises a cylindrical canister complete with a circular cap and a breathable disk comprised of a ring-shaped mount of support material, it should be understood that devices comprised of differently shaped and/or sized components can also be formed according to the method disclosed herein.

Figure 5A:
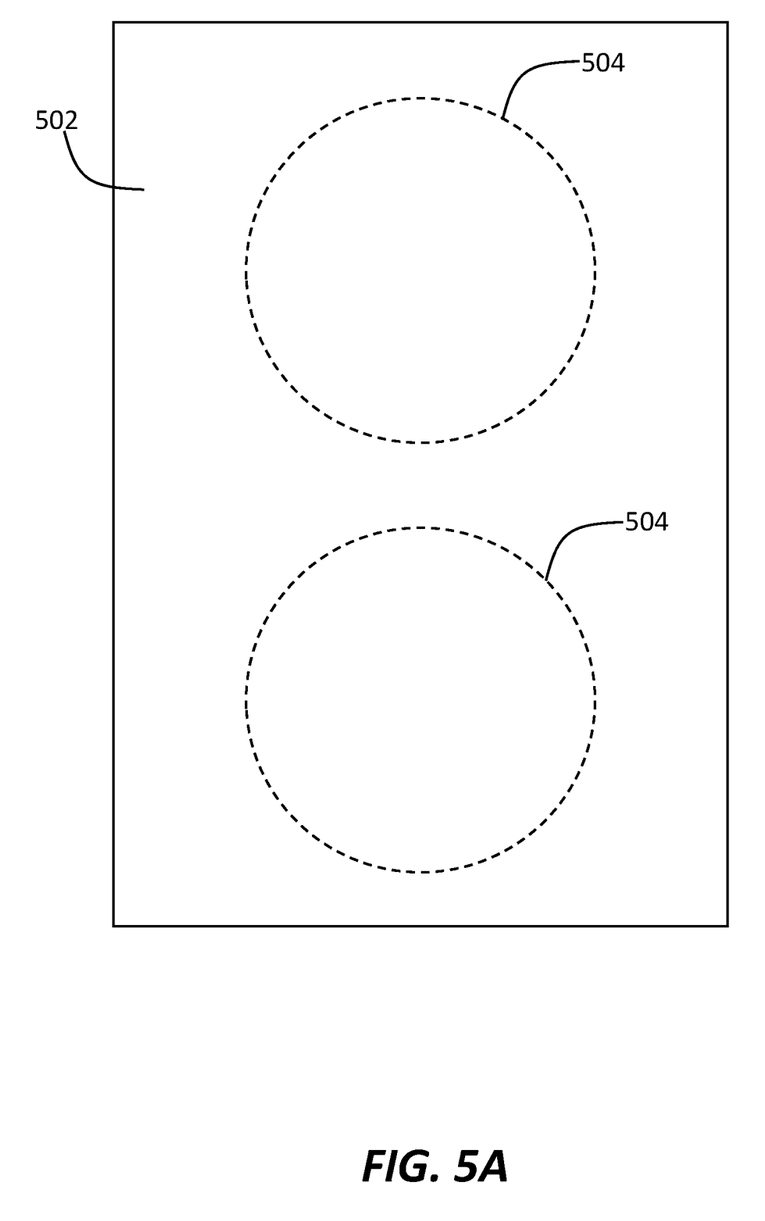
FIG. 5A is a plan view of an initial step of cutting a ring of support material implemented pursuant to an example method of manufacturing a cylindrical scent device in accordance with embodiments of the present disclosure.

FIG. 5A illustrates an initial step that may be implemented according to example methods of producing the scent devices described herein. From a stock of sheet material 502, one or more cutouts 504 can be removed and discarded by cutting along the dashed lines. The sheet material 502 can comprise pulp board, paper board, cardboard, foam or other materials, which may be substantially rigid. The remaining sheet material 502, i.e., lacking the cutouts 504, may define the inner diameter of two ring-shaped mounts or backing structures used to form two breathable inserts, each in the form of a disk. The cutouts 504 are circular in this example to match a cylindrical container holding a fill material, but as mentioned above, the shape of the container, and thus the cutouts, can vary. The diameter of the cutouts 504 can also vary, ranging from less than about 1.75 in. to about 2 in., about 2 in., about 2.25 in., about 2.50 in., about 2.75 in., about 3 in., about 3.25 in., about 3.5 in., about 3.75 in., about 4 in., about 4.25 in., about 4.5 in., about 4.75 in., about 5.0 in., greater than about 5.0 in., or any diameter therebetween. The number of cutouts 504 is shown for illustration purposes only. Greater or fewer cutouts 504 can be removed depending on surface area of available sheet material 502.

The sheet material 502 can be cut using a die apparatus. The die apparatus can be a rotary die, a flat die or any other form of die or press, including turret and rail-type punch presses. The die apparatus can be operated via automated or manual control. In some embodiments, the sheet material 502 may be supplied on a roll, making it particularly compatible with a rotary die apparatus. The sheet material 502 can vary in cross-sectional thickness, ranging from less than about 0.01 in., about 0.01 in., about 0.02 in., about 0.03 in., about 0.04 in., about 0.05 in., about 0.06 in., about 0.07 in., about 0.08 in., about 0.09 in., about 0.10 in., greater than about 0.10 in., or any thickness therebetween.

Figure 5B:
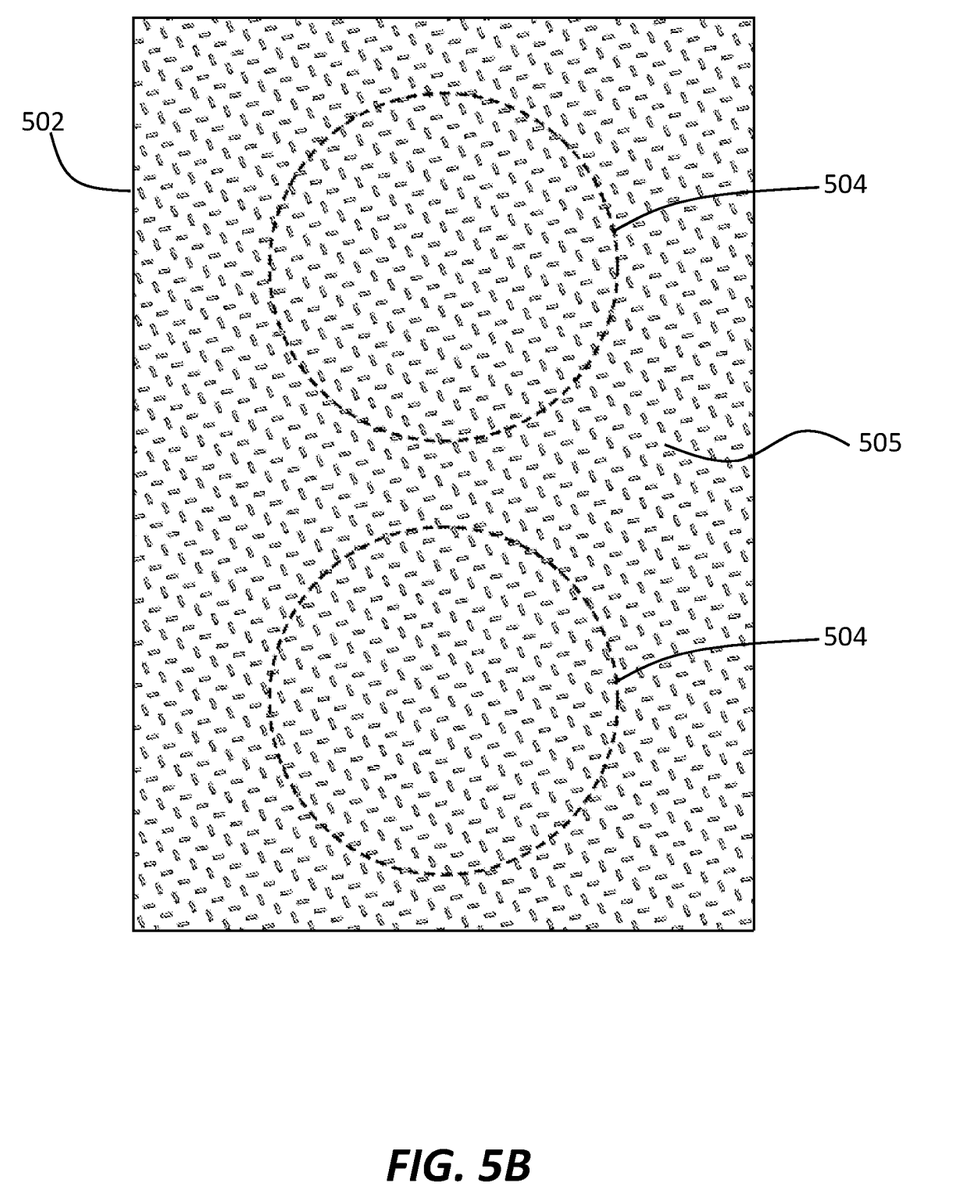
FIG. 5B is a plan view of a lamination step implemented after cutting the inner diameter of the ring of support material.

FIG. 5B illustrates a subsequent step, in which a breathable material 505 is laminated to the sheet material 502, such that the breathable material covers one side of the sheet material 502 and spans the circular apertures defined by the initial cutouts 504. In some embodiments, both sides of the sheet material 502 can be laminated with the breathable material 505. In other examples, lamination of the breathable material 505 may be supplemented and/or replaced by a different method of attachment. For example, the support material 502 may comprise an adhesive on one or both sides. This adhesive may be sufficient to adhere the breathable material 505 to the support material 502. As provided herein, the breathable material 505 may comprise a woven fabric or one more different breathable materials, non-limiting examples of which may include threaded polymers and/or mesh.

Figure 5C:
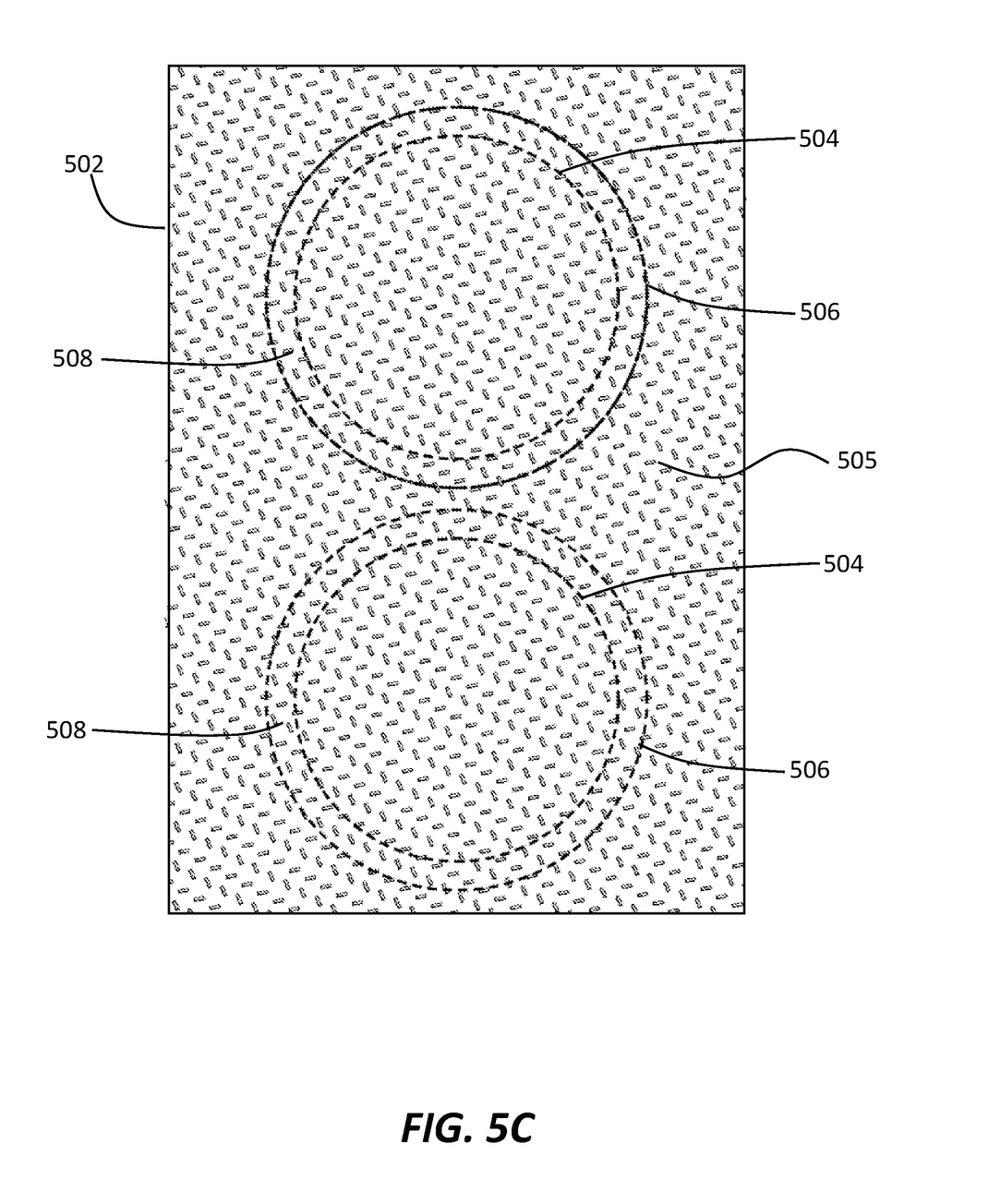
FIG. 5C is a plan view of a step of cutting the outer diameter of the laminated support material to form a breathable disk.

FIG. 5C shows a step in which the sheet material 502 and breathable material 505 are cut together, this time along concentric cutting lines 506 of a larger diameter than the original cutouts 504 to define the ring-shaped mounts 508 of the breathable insert. The same die apparatus can be used to implement this step.

Figure 5D:
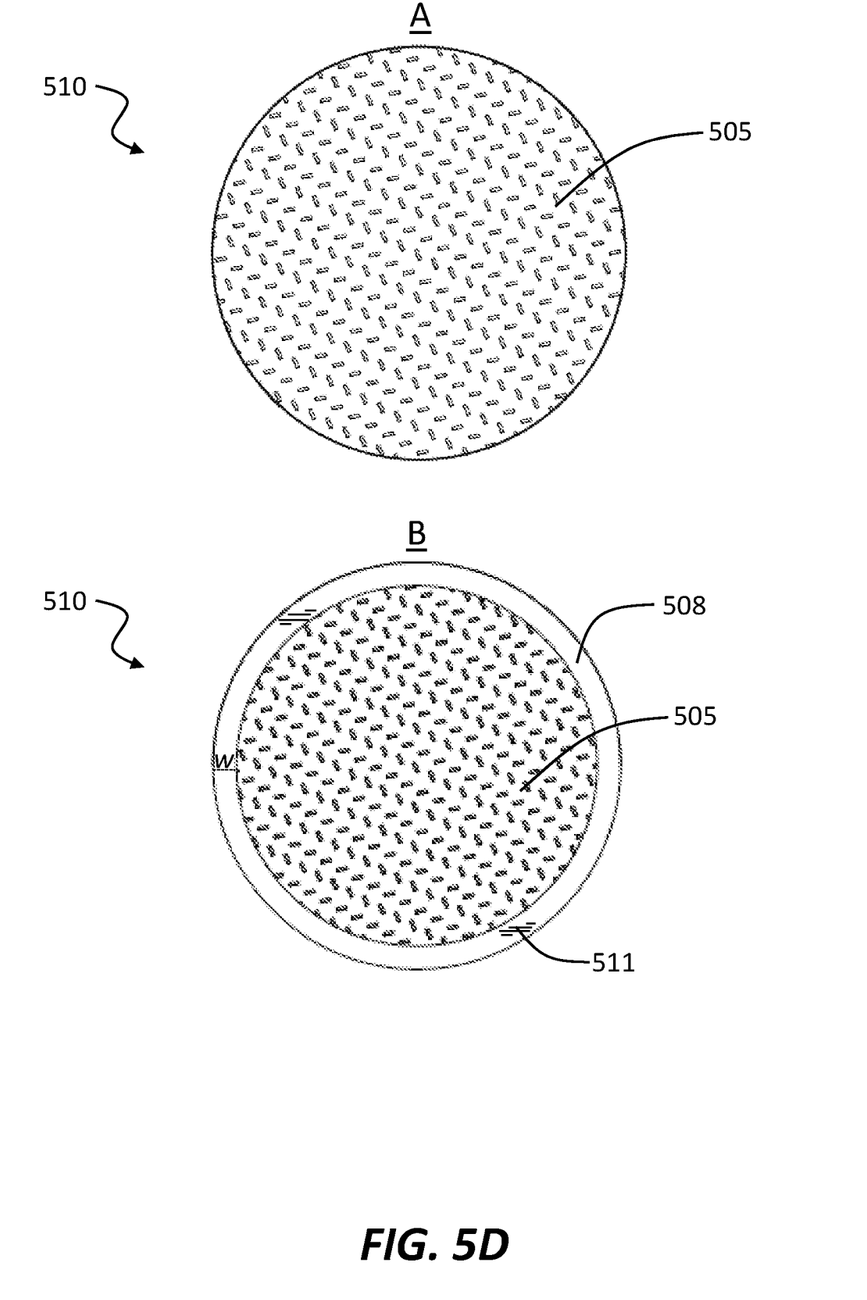
FIG. 5D is a plan view of both sides of a breathable disk formed after implementing the steps shown in FIGS. 5A-5C and discarding the unused support material.

FIG. 5D shows opposite sides of a breathable insert in the form of a breathable disk 510 created by the sequential cuts and lamination steps illustrated in FIGS. 5A-5C, after removal of the extraneous support material 502 and breathable material 505, i.e., the material not defined within cutting lines 506. As shown, one side of the breathable disk 510, designated as side A for illustration purposes, may be entirely covered by the breathable material 505. Side A represents the laminated side of the breathable disk 510 in this example. The opposite side, side B, represents the side that was not laminated. Accordingly, the ring mount 508 comprised of the support material 502 is visible on side B, but not side A. The ring mount 508 defines a central aperture, which is circular in the embodiment shown, to allow passage of aromatic compounds, odors and/or moisture through the breathable material 505 spanning the aperture.

The outer diameter of the ring mount 508, and thus the breathable disk 510, may approximately match, or be slightly greater than, the diameter of the container with which the ring mount 508 will be eventually coupled, such that the diameter of the container is greater than the diameter of the initial cutouts 504, but less than the diameter of the circles defined by the second cutting lines 506. Embodiments of the ring mounts 508 may have an outer diameter ranging from less than about 2.25 in. to about 2.5 in., or about 2.5 in., about 2.75 in., about 3 in., about 3.25 in., about 3.5 in., about 3.75 in., about 4 in., about 4.25 in., about 4.5 in., about 4.75 in., about 5.0 in., about 5.25 in., about 5.5 in., greater than about 5.5 in., or any diameter therebetween.

The width w of the ring mounts 508 may vary depending on a plurality of factors, including the level of support required by the breathable material comprising the breathable disk 510, the dimensions of the container and cap into which each ring is inserted, and/or the desired rate of scent release and/or odor/moisture absorption. For example, the width w may be greater for containers having a larger diameter to provide the structural support necessitated by a breathable insert having greater surface area. The width w may also be increased to slow the rate of scent release by decreasing the surface area of the breathable insert through which a scent can pass through. In various embodiments, the width w may range from less than about 0.2 in., about 0.2 in., about 0.25 in., about 0.3 in., about 0.35 in., about 0.4 in., about 0.45 in., about 0.5 in., about 0.55 in., about 0.6 in., about 0.65 in., about 0.70 in., about 0.75 in., greater than about 0.75 in., or any width therebetween.

As further shown in FIG. 5D, the ring mount 508 may have a surface adhesive 511 on one or both sides. The adhesive 511 can be applied to or formed with the stock material 502 before cutting, or applied after one or more cuts are made. In embodiments, the adhesive 511 can be a pressure-sensitive adhesive. In embodiments featuring a pressure-sensitive adhesive, the support material 502 comprising each ring mount 508 can be pressed directly against the breathable material 505 to strengthen the bond between the two components, before or after lamination, which may prevent or minimize slippage of the breathable material 505. As mentioned above, both sides of the ring mount 508 may have an adhesive 511. Accordingly, side B of the ring mount 508 may have exposed adhesive 511 ready for bonding to an additional surface, e.g., the rim of a container comprising a fill material. Attachment of the ring mount 508 to the container may be achieved before or during coupling of the container with a cap. In some embodiments, the breathable disk 510 may include a layer of breathable material 505 sandwiched between two ring mounts 508, for example in embodiments requiring enhanced structural support.

Figure 5E:
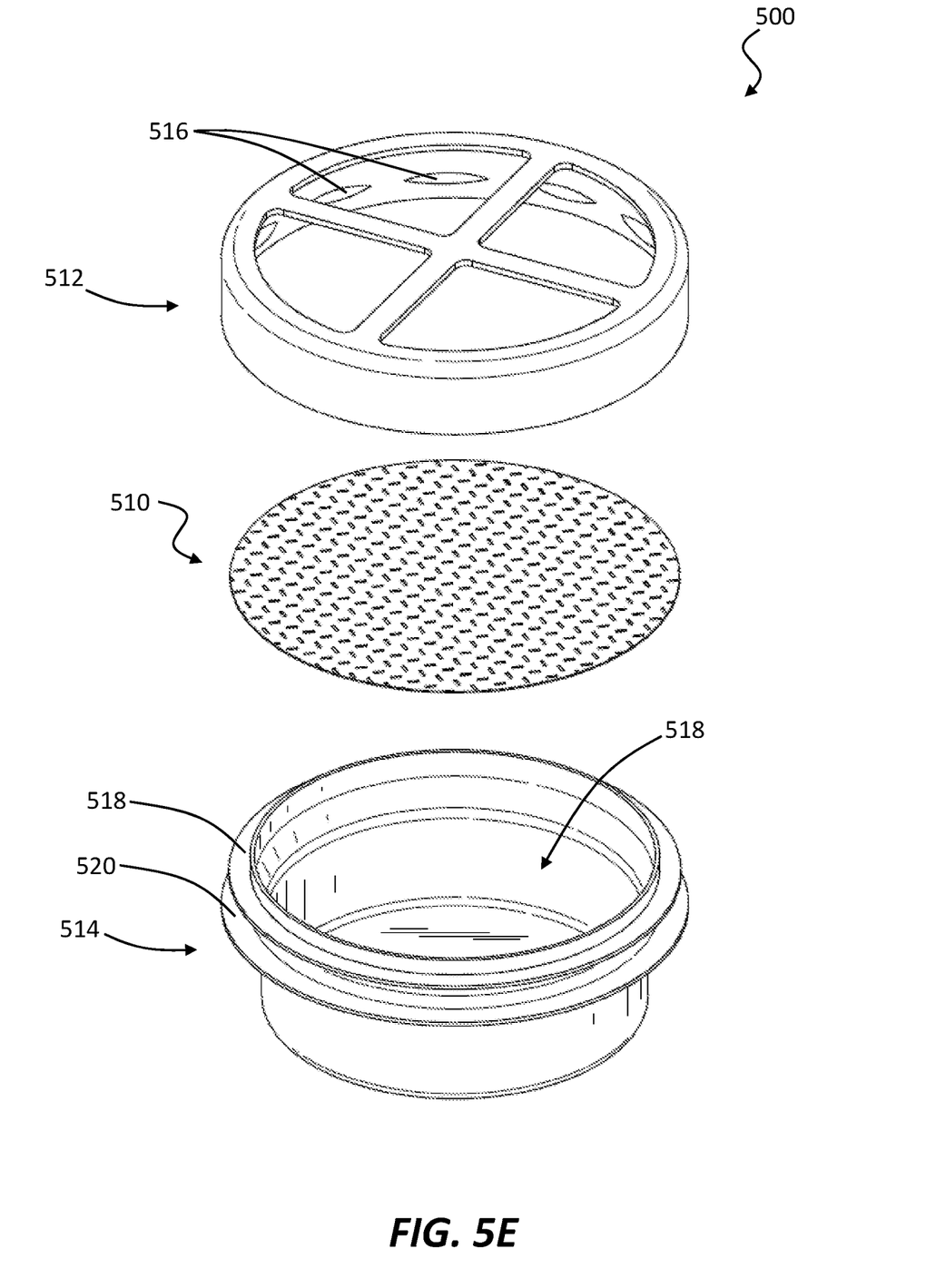
FIG. 5E is an exploded view of a scent device, showing a container, the breathable disk shown in FIG. 5D, and a cap with vents.

FIG. 5E is an exploded view of an unfilled scent device 500, showing a breathable insert in the form of a breathable disk 510 (side A), along with a cap 512 and a container 514. A series of protrusions 516 are visible along an inner surface of the cap 512. The protrusions 516 may be urged over a circumferential lip portion 518 defined by an exterior surface of the container 514 to couple the container 514 with the cap 512 via a snap-fit mechanism. As further shown, the container 514 defines an internal volume 518 configured to receive a fill material and a circumferential ledge 520 configured to contact a circumferential portion of the cap 512. The container 514 may be formed from one or more polymer compositions in some examples via various techniques, such as molding or 3-D printing.

Figure 5F:
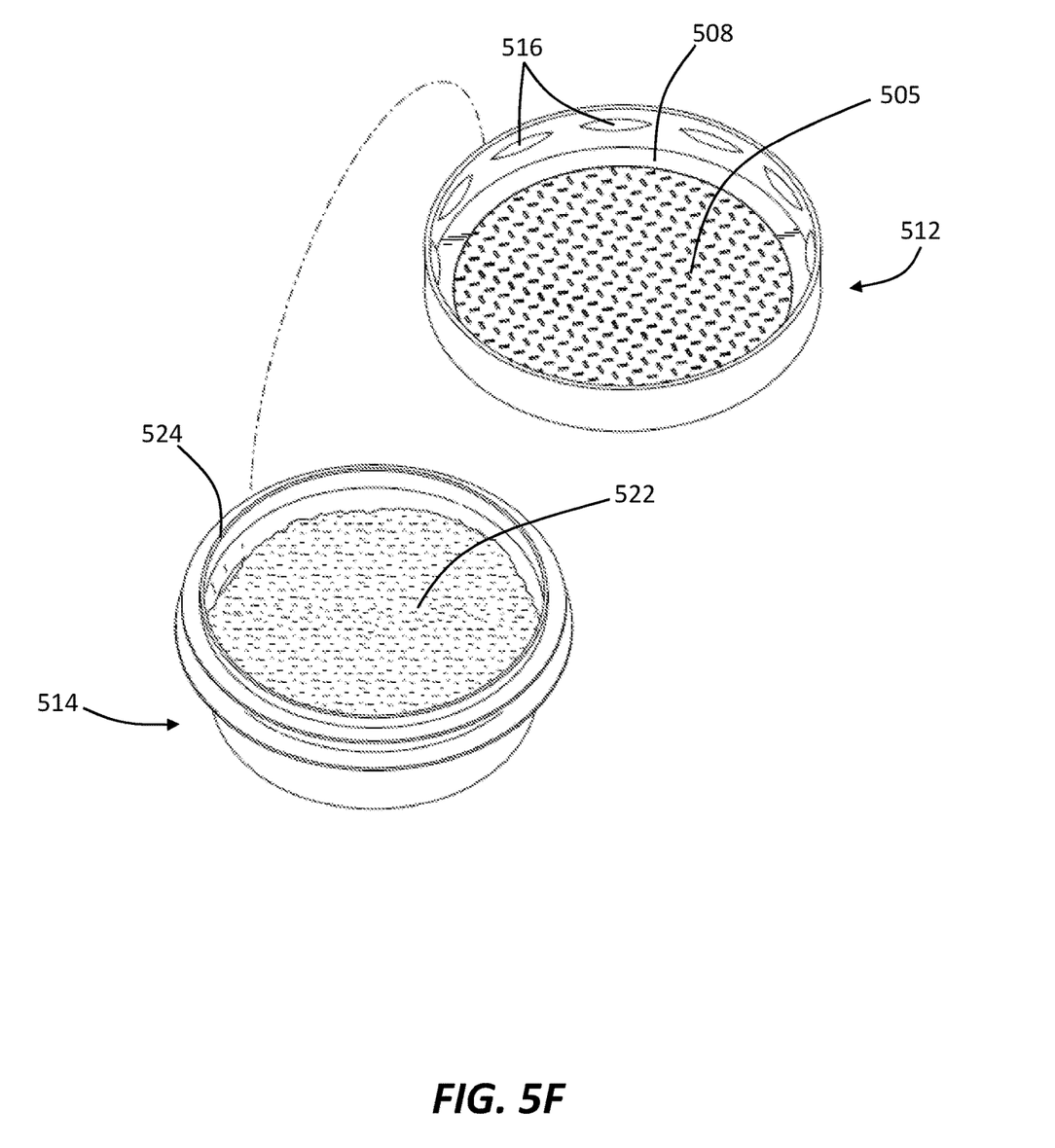
FIG. 5F is a perspective view of the container shown in FIG. 5E after depositing a fill material therein, along with an underside of the cap and breathable disk after coupling the two components together.

Before, during or after forming the breathable disk 510, a scented, scent-controlling, and/or moisture-absorbing fill material 522 can be deposited within the volume 518 defined by the container 514, as shown in FIG. 5F. The container 514 can be substantially filled with the material 522, or to any user-desired level. After depositing the fill material 522 into the container 514, the cap 512 and breathable disk 510 can be coupled with the container. As shown, the exposed side of the ring mount 508 can face the container 514, such that a lip 524 of the container 514 directly contacts the ring mount 508. In addition to providing structural support to the breathable material 505, the ring mount 508 may prevent or minimize leakage to and from the container 514 by forming a seal between the container and the cap. The thickness of the ring mount 508, along with its relatively soft or impressionable texture, can increase the level of friction and eliminate gaps between the cap 512, container 514, and breathable disk 510 around the perimeter of the device 500, which may prove critical in the event that the lip 524 includes uneven surfaces or notches due to manufacturing imperfections and/or damage.

Figure 5G:
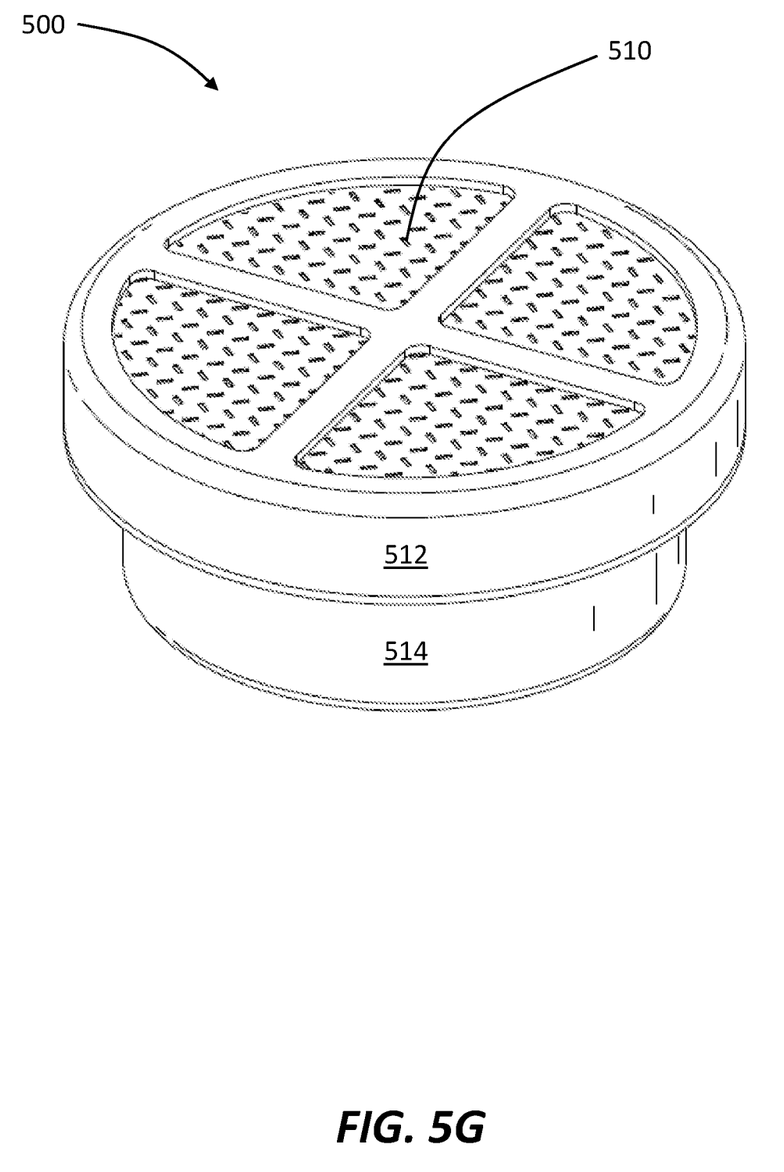
FIG. 5G is a perspective view of an assembled scent device.

FIG. 5G shows a fully assembled scent device 500. In the example shown, the cap 512 has a wider diameter than the container 514. The relative sizes of the two components may facilitate actuation of the snap-fit mechanism by enabling a user to pry the cap 512 from the container 514. Embodiments may feature different dimensions, such that the container 514 and cap 512 define similar or identical diameters.

Figure 6:
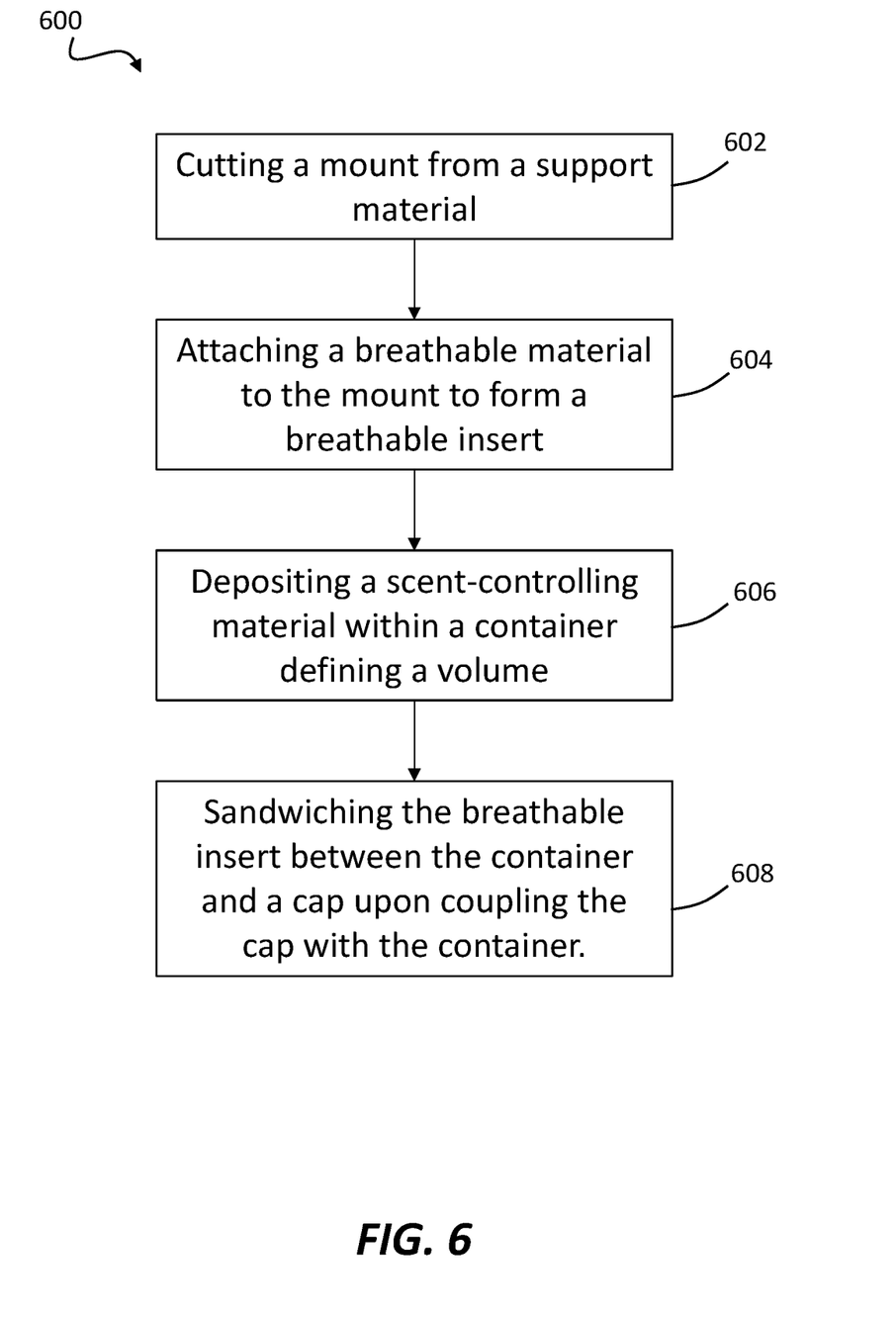
FIG. 6 is a flow chart depicting a method of manufacturing a scent device in accordance with principles of the present disclosure.

FIG. 6 is a flow diagram of a method of forming a scent device in accordance with principles of the present disclosure. The example method 600 shows the steps that may be utilized, in any sequence, to form a scent device for indoor or outdoor use.

In the embodiment shown, the method 600 begins at block 602 by "cutting a mount from a support material." At block 604, the method involves "attaching a breathable material to the mount to form a breathable insert." At block 606, the method involves "depositing a scent-controlling material within a container defining a volume." At block 608, the method involves "sandwiching the breathable insert between the container and a cap upon coupling the cap with the container."

As used herein, the term "about" modifying, for example, the quantity of a component in a composition, concentration, and ranges thereof, employed in describing the embodiments of the disclosure, refers to variation in the numerical quantity that can occur, for example, through typical measuring and handling procedures used for making compounds, compositions, concentrates, or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

Similarly, it should be appreciated that in the foregoing description of example embodiments, various features are sometimes grouped together in a single embodiment for the purpose of streamlining the disclosure and aiding in the understanding of one or more of the various aspects. These methods of disclosure, however, are not to be interpreted as reflecting an intention that the claims require more features than are expressly recited in each claim. Rather, as the following claims reflect, inventive aspects lie in less than all features of a single foregoing disclosed embodiment, and each embodiment described herein may contain more than one inventive feature.

Although the present disclosure provides references to preferred embodiments, persons skilled in the art will recognize that changes may be made in form and detail without departing from the spirit and scope of the inventive.

What is claimed is:

1. A method of forming a scent device, the method comprising
cutting a mount from a support material;
attaching a first surface of a breathable material, opposite a second surface of the breathable material, to the mount to form a breathable insert, wherein the second surface does not contact the mount;
depositing a scent-controlling material within a container defining a volume; and
sandwiching the breathable insert between the container and a cap upon coupling the cap with the container, wherein sandwiching the breathable insert between the container and the cap comprises applying a side of the mount opposite the breathable material to a lip portion of the container.

2. The method of claim 1, wherein the scent-controlling material comprises a composition configured to absorb moisture, absorb odor, emit a scent, or combinations thereof.

3. The method of claim 1, wherein the breathable material comprises a non-woven fabric.

4. The method of claim 1, wherein the support material comprises pulp board, paper board and/or foam.

5. The method of claim 1, wherein attaching a first surface of the breathable material to the mount comprises laminating the breathable material to the mount.

6. The method of claim 1, wherein cutting the mount from the support material comprises using a die apparatus to cut the mount from a roll of the support material.

7. The method of claim 1, wherein the breathable insert has a cross-sectional thickness of about 0.01 to about 0.05 inches.

8. The method of claim 1, wherein the support material is substantially rigid.

9. The method of claim 1, wherein the support material comprises a double-sided adhesive.

10. The method of claim 1, wherein coupling the cap with the container comprises snap-fitting the cap to the container.

* * * * *